United States Patent
Eng et al.

[11] Patent Number: 6,056,756
[45] Date of Patent: May 2, 2000

[54] FEMORAL TENSING AND SIZING DEVICE

[75] Inventors: Lisanne Eng, North Attleboro; Dennis Colleran, Plainville; John Slamin, Wrentham, all of Mass.

[73] Assignee: Johnson & Johnson Professional, Inc., Rayham, Mass.

[21] Appl. No.: 09/132,279

[22] Filed: Aug. 11, 1998

[51] Int. Cl.$^7$ ...................................................... A61F 5/00
[52] U.S. Cl. ................................ 606/87; 606/88; 606/90; 606/96
[58] Field of Search ................................ 606/86, 87, 88, 606/90, 96, 102

[56] References Cited

U.S. PATENT DOCUMENTS

| | | | |
|---|---|---|---|
| 4,567,886 | 2/1986 | Petersen | 128/92 H |
| 4,759,350 | 7/1988 | Dunn et al. | 128/92 VW |
| 5,484,446 | 1/1996 | Burke et al. | 606/87 |
| 5,540,696 | 7/1996 | Booth, Jr. et al. | 606/88 |
| 5,597,379 | 1/1997 | Haines et al. | 606/88 X |
| 5,669,914 | 9/1997 | Eckhoff | 606/88 |
| 5,688,280 | 11/1997 | Booth, Jr. et al. | 606/88 |
| 5,735,904 | 4/1998 | Pappas | 606/88 X |
| 5,776,137 | 7/1998 | Katz | 606/88 |
| 5,860,980 | 1/1999 | Axelson, Jr. et al. | 608/88 |
| 5,911,723 | 6/1999 | Ashby et al. | 606/88 |

FOREIGN PATENT DOCUMENTS

| | | | |
|---|---|---|---|
| 0380451 | 8/1990 | European Pat. Off. | 606/88 |

OTHER PUBLICATIONS

Johnson & Johnson Orthopaedics—"Revision Surgery for Failed Total–Knee Replacement", SP2–008, J&JP, Inc. 1997.

Johnson & Johnson Orthopaedics—"Primary Cruciate–Retaining Procedure", SP2–001, J&JP, Inc. 1996.

*Primary Examiner*—Jeffrey A. Smith
*Attorney, Agent, or Firm*—Nutter, McClennen & Fish LLP

[57] ABSTRACT

A tool for preparing a bone end for prosthetic joint replacement. The tool rests on a resected end of one bone of an articulating joint set, and includes a jack assembly for supporting an opposing bone of the set in flexion while the bone ends remain attached together by ligaments. The jack pivotally supports the opposing bone and raises it to the spacing of the intended prosthesis to allow the surgeon to balance soft tissue tension. This support allows the bone to rotate under the tension of the connecting ligaments, into natural alignment while a template carried by the jack assembly lies against the prepared end, so subsequent cuts are in correct rotational alignment and the bone enjoys a natural posture when the joint components are attached. Preferably, a sizing jig in the tool contacts the bone to determine an offset, and a positioning block coupled to the sizing jig confirms the size, and positions drill holes on the bone surface contacted by the jig to set the orientation for attaching a cutting block. The sizing jig may include a template for indicating the size of a required joint component, and the jack may support the bone on an intramedullary rod. In one embodiment, the jack moves a gimballed assembly which fits about the intramedullary rod, allowing the template to rest flat against the resected bone end. Preferably, the device places drill holes in position for a cutting block to fit a femoral end component of a prosthetic knee.

6 Claims, 5 Drawing Sheets

FEMORAL TENSING AND SIZING DEVICE

FIELD OF INVENTION

The present invention relates to tools and jigs for laying out machine cuts to prepare a bone for receiving a correctly sized and aligned prosthetic component, such as prosthetic knee.

BACKGROUND OF THE INVENTION

The surgical preparation of bone endings for receiving prosthetic knee joints for a total knee replacement is generally a complex procedure, particularly when ligaments remain attached, or when osteoarthritic changes to the joint have distorted the normal, more symmetric articulation geometry of the joint or bone. In general, it is necessary to perform soft tissue balancing and numerous specially aligned cuts at the bone ends in order to install the prosthetic components with correct spacing and alignment to prevent improper kinematics from arising as the joint rotates in use, and prevent the occurrence of accelerated wear patterns or possible joint dislocation.

A number of bone cuts are made to effect the placement and orientation of the femoral component of the prosthesis, and to determine and form the joint gaps in extension and flexion. The size and shape of these two gaps affect final orientation of the prosthesis, as well as joint tensioning and clearances. With respect to their effect on final orientation, the flexion gap is related to internal/external orientation of the femur, while the extension gap is related to the varus/valgus orientation of the femur.

Generally, these cuts are formed so that in extension the joint gap is perpendicular to the mechanical axis of the femur, while in flexion the joint gap is such as to place the femoral component in either neutral or external rotation and assure proper patellar tracking with the femoral component. Furthermore to fit the femoral component the gaps created by the bone resections in both flexion and extension should be rectangular.

Typically this requires a number of measurement steps and cutting or fitting steps, often with additional small adjustment cuts to achieve the fmal bone preparation. However it is difficult to devise a jig which dependably sets the degree of femoral rotation, because landmarks may be inconsistent or obscure. In general, the surgeon must exercise judgment as the various cuts are made. Also the steps in reaching a determination will vary depending upon the initial landmarks used for setting preliminary resections, both as a matter of the surgeon's preferred procedure and as constrained by any patient-specific features or disease.

Accordingly, it would be desirable to provide a tool to simplify procedures for performing preparatory bone cuts or markings for preparing the bone to receive a prosthetic joint component.

SUMMARY OF THE INVENTION

A tool in accordance with the present invention lays out resection or alignment features for prosthetic joint replacement. The tool rests on a resected end of one bone of an articulating joint set, and includes a jack for pivotally supporting an opposing bone of the set while the two bone ends remain attached together by ligaments. The jack raises the opposing bone in flexion to the spacing of the intended prosthesis to allow the surgeon to balance soft tissue tension. This support allows the bone to rotate under the tension of the connecting ligaments into natural alignment, so that a template carried by the jack assembly for initially laying out drill holes, a saw cut or the like, lies against the prepared end with the bone in that orientation, thereby assuring a correct rotational alignment of the machined bone when the joint components are attached. Preferably, a sizing jig in the tool contacts the bone to determine an offset, and a positioning block coupled to the sizing jig positions drill holes on the bone surface contacted by the jig. The sizing jig may include a template for indicating the size of a required prosthetic joint component, as well as one or more accessories for confirming or adjusting the size indicated on the template with respect to other landmarks. The jack may lift a gimballed collar that fits about on intramedullary rod to support the bone, thus allowing the marking or fitting components to pivot to the appropriate varus/valgus plane. The drill holes may set a position for a standard cutting block to fit a femoral end component.

DETAILED DESCRIPTION OF ILLUSTRATIVE EMBODIMENT

The present invention is a tool which simplifies the procedure of preparing the distal femoral end for a prosthetic implant by allowing the surgeon to set soft tissue tension, size the femur, and size the flexion gap using a single instrument. The mechanical arrangement of various components of the tool in a prototype embodiment 50 will be appreciated from discussion of the figures below, illustrating its structure and operation.

Figure 1:
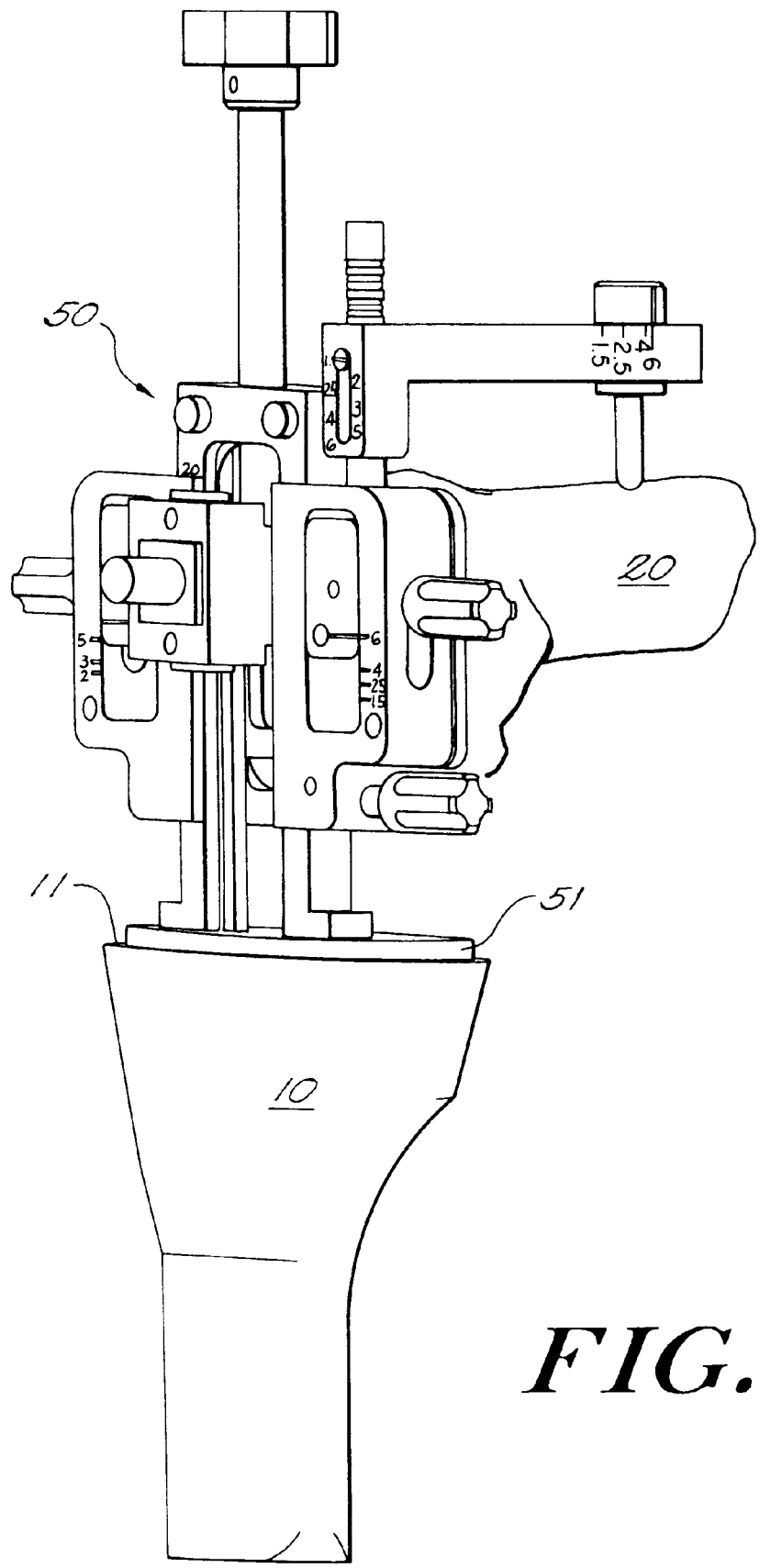
FIG. 1 illustrates the tibia and femur of a leg with an embodiment of the tool according to the present invention attached to the femur.

As shown in FIG. 1, the tool is intended for use during surgery, and has a base 51 which rests on the proximal resected tibial cut 11 of a tibia 10 to support the femur 20. By way of overview, the tool is used once the surgeon has performed the proximal tibial cut, made the distal femoral cut, and freed up the collateral ligaments, so that the extension gap between the end faces of the tibia and femur which are to receive the prosthetic joint components has been set. In general, this gap in extension is checked using sizing blocks, and is set for one representative system to be approximately 17 millimeters or greater; the spacing is set to accommodate the combined vertical thicknesses of the articulating femoral component, the tibial tray, and an insert having an upper articulation surface.

Figure 2:
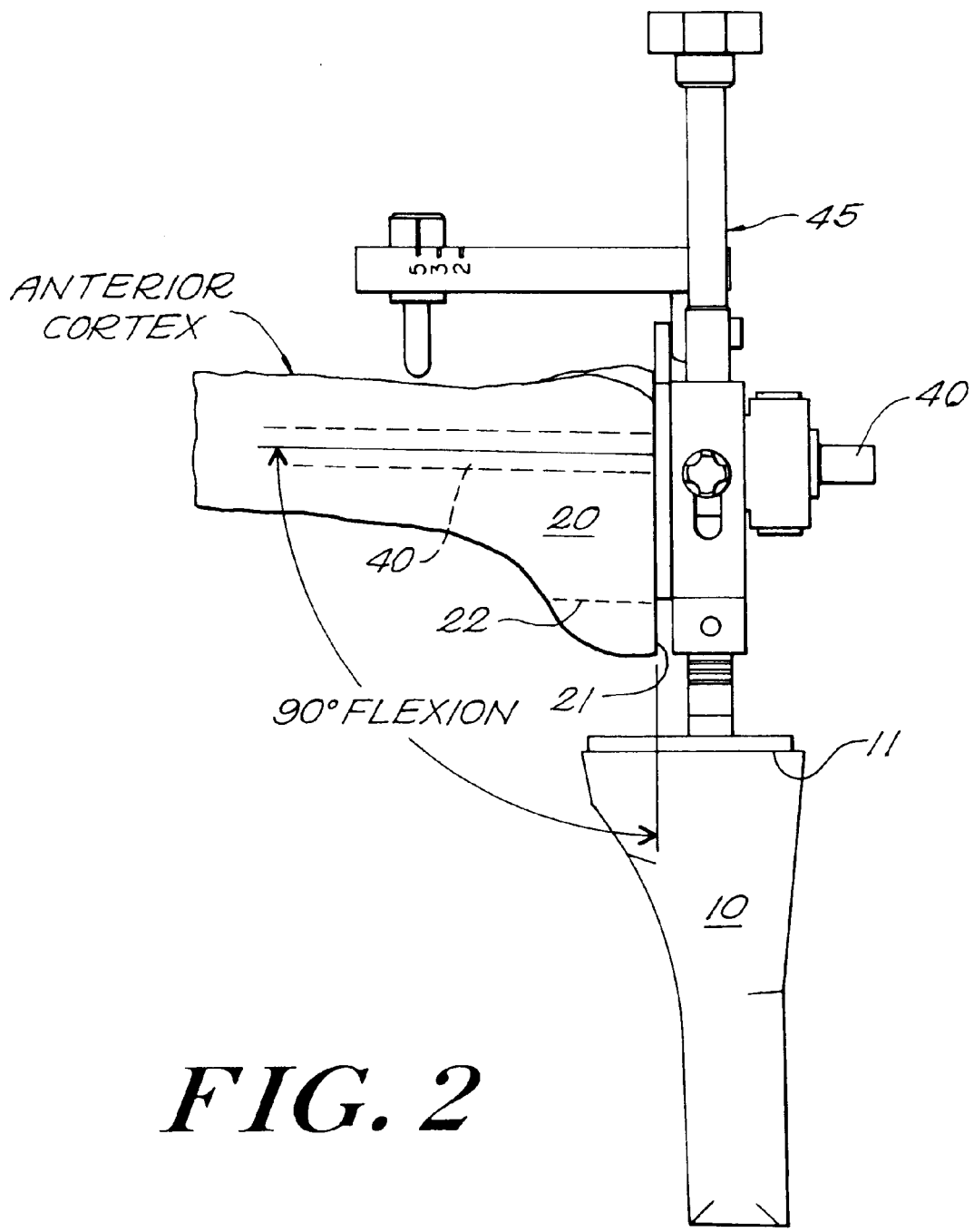
FIG. 2 is a side view of the tool shown in FIG. 1 illustrating relevant bone features.

Once these preparatory cuts have been made, the exposed bones are placed in flexion and the tool 50 is used to support the femur 20, with the base 51 of the tool set on the proximal resected tibial end 11, while a subassembly slides against the distal resected femoral end 21. As best seen in the side view of FIG. 2, in accordance with a principle aspect of the present invention, the tool 50 supports the femur 20 on an intramedullary rod 40 which is raised or lowered by a jack assembly indicated generally by 45 while the surgeon adjusts the soft tissue tension in flexion. The femur 20 may pivot with the rod under the influence of tension of the medial and lateral ligaments, so that when soft tissue balancing is achieved, the bone will rotate into a natural position. Other portions of the tool carried by the jack assembly then cooperate to set marks or positioning features for attaching a conventional cutting block to then perform the posterior femoral cut, indicated schematically by dashed line 22 in the figure, which sets the flexion gap. Operation of the tool assures that the flexion gap so defined places the femoral component in either neutral or external rotation, thus assuring that proper patella tracking will occur. This operation will be more fully understood from a more detailed discussion of the tool and its structural features, a prototype embodiment of which is illustrated in FIG. 3.

Figure 3:
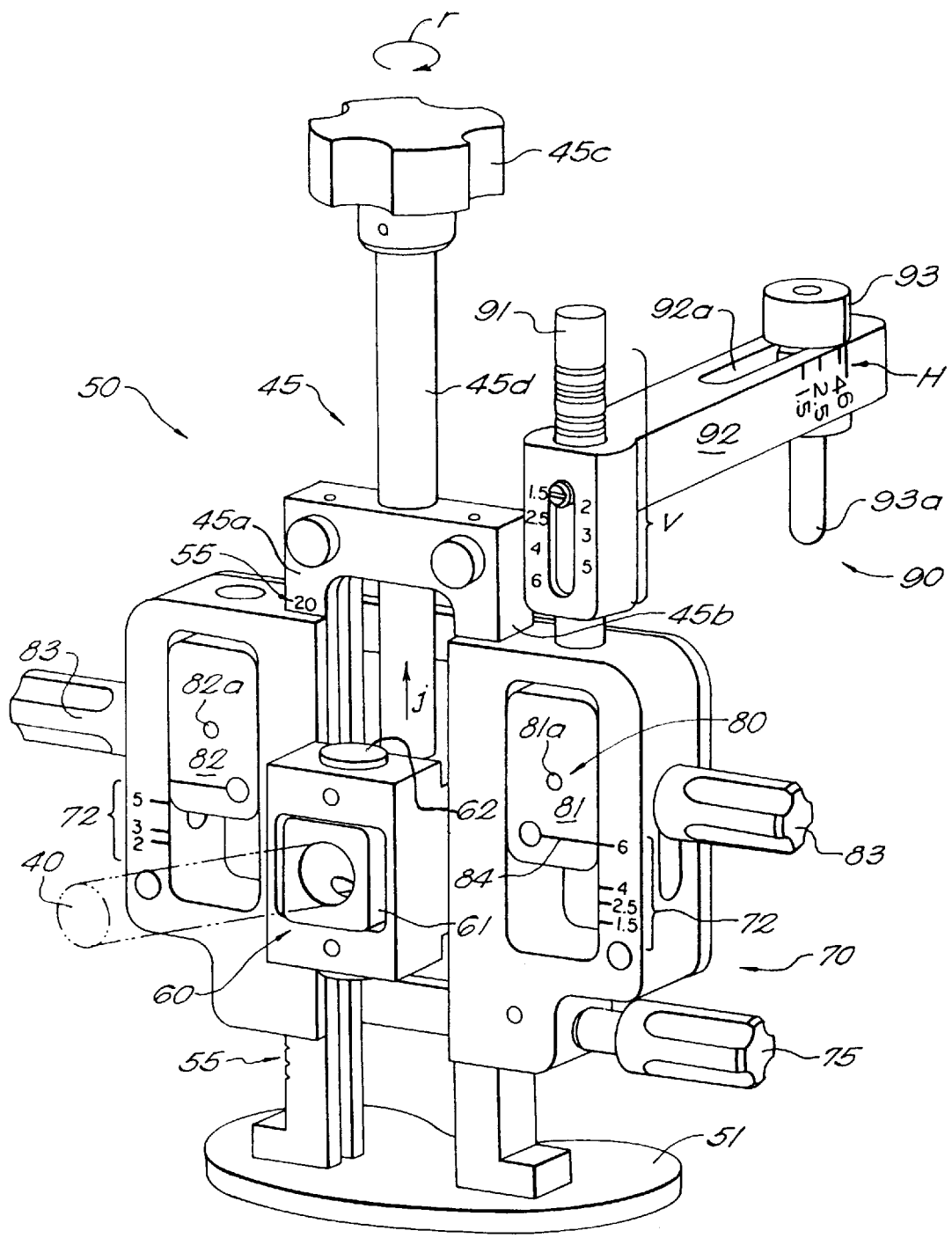
FIG. 3 is a perspective view of the prototype embodiment shown in FIGS. 1 and 2.

As shown in FIG. 3, the tool 50 includes a jack assembly 45 which extends upward from a base or support plate 51. The jack assembly moves a lifting carriage 60 between two support posts 45a, 45b along a vertical direction, while a sizing block 70 is configured to be manually moved up and down the support posts of the jack assembly. The lifting carriage 60 lifts the intramedullary rod 40 to set the height of the femur, and the sizing block 70 slides along the same axis so that it may be readily aligned with the femur at the distal end. Within the sizing block 70, a positioning template 80 including first and second drill guide blocks 81, 82 which are rigidly connected to each other by a thin bridge plate 86 (shown in FIG. 6) slide up and down as a unit against the distal femoral surface to position the drill guides 81a, 82a respectively. The drill guide or template 80 may be locked in position within the sizing block 70 by locking thumb screws 83. Also, the guide or template 80 connects to a preferably removable cortex hook assembly 90 comprising a vertical post 91 which rotates about its axis in a pair or aligned support holes (not numbered) in the sizing block 70 and drill guide 80, and carries a vertically adjustable positioning arm 92 to position a pin 93 against the anterior femoral cortex. The positioning arm 92 slides up and down with detents on the post 91 to indicate (as a component size) the vertical height of the femoral surface, and stylus 93 slides back and forth in a slot 92a of the arm to position its tip 93a behind the condyles on the surface of the femur. Corresponding size markings are graduated on each of posts 91 and arm 92 to show the size of the femur. Correspondingly, graduations for the available femur articulation components appear on the sizing block 70 at regions 72. Thus, the graduated readings of assembly 90 confirm or indicate a discrepancy with the size set on the sizing block 70, and thus allow the size to be adjusted as the assembly is positioned.

The tensioning and sizing device of FIG. 3 is used during a surgical procedure as follows. First the tibial plateau and distal femur are resected and preliminary soft tissue balancing is carried out. The size of the gap between opposed resected bone endings is assessed with the leg in extension using spacer blocks which correspond to the specific tibial insert thicknesses which are to be used. Then, with the knee in 90° flexion, the support base 51 of the tool is placed on the resected tibial surface, and an intramedullary rod 40 is inserted into the intramedullary canal of the femur, and through the horizontal bore in the carriage 60.

As shown, the lifting carriage 60 receives the intramedullary rod 40 in a block 61 which is mounted to pivot about a vertical axis by pin 62 so that the face plane of the entire assembly, i.e. the vertically-disposed plane on the side opposite to that illustrated of the sizing block drill guide, may rest flush against the resected distal femur with which the rod makes the appropriate varus/valgus angle. With the rod centrally supported by the gimballed holding block 61, turning the top knob 45c rotates the jack screw 45d and lifts the carriage 60, thus elevating the gimballed carrier so as to spread the tibia from the femur and tense the collateral ligaments. This tenses the collateral ligaments in the flexion position, and the size of the flexion gap is then matched to the previously assessed extension gap, by manually sliding the sizing block 70 vertically. Its position is indicated by calibration markers 55 on the posts 45a, 45b of the jack frame, which are preferably graduated in millimeters corresponding to the previously assessed cumulative thickness of the prosthesis, tray and insert used to set the initial extension gap. A thumbscrew 75 bears against post 45b to fix the sizing block 70 in position at the selected graduation or flexion gap, and the surgeon may adjust the soft tissue tension in the set position.

The femur size is set next, by sliding the drill guide 80 vertically within the sizing block 70 to line up with one of the markings 72a, 72b on the front (anterior) face of the sizing block 70 corresponding to the specific femoral component sizes. This may be set to an initial or estimated size. The guide is locked into place by tightening two thumb screws 83 when the graduation reads the desired implant size. An adjustable stylus assembly 90 having components 91, 92, 93 is placed into the drill guide and through the sizing block, and is used to check the fit of the chosen implant size. A post 91 supports an arm 92 in which a stylus 93 is adjustably positioned to contact the anterior surface of the femur. For the correct size, the dimensions of post 91 and positioning arm 92 are such that this same size will be read off on the vertical and horizontal graduation scales of that assembly when the tip 93a of the stylus just touches the anterior cortex of the femur. If this is not the case, then a different size prosthesis may be considered to assure a better fit, and the guide 80 may be re-set accordingly. When the proper fit is achieved, holes are drilled into the distal resected femur using the drill positioning guide holes 81a, 82a. The device is then removed and surgical technique proceeds using standard A/P resection blocks pinned in the two drill holes so made.

Advantageously, as the femur is moved vertically relative to the resected tibia, it will assume a natural orientation which is either in neutral or external rotation by virtue of the freely pivotal support of the rod 40; thus the flexion gap determined by the placement of the drill holes in the distal face will assure that the prosthesis is fitted on the femur with the desired rotational alignment. Furthermore, the tensioning tool of the present invention allows the surgeon to conveniently adjust the soft tissue tension in flexion while sizing the femur and determining the cutting block position. The jack assembly supports the sizing block flush against the end of the femur and checks the prosthesis size in two dimensions against the anterior cortex.

Figure 4:
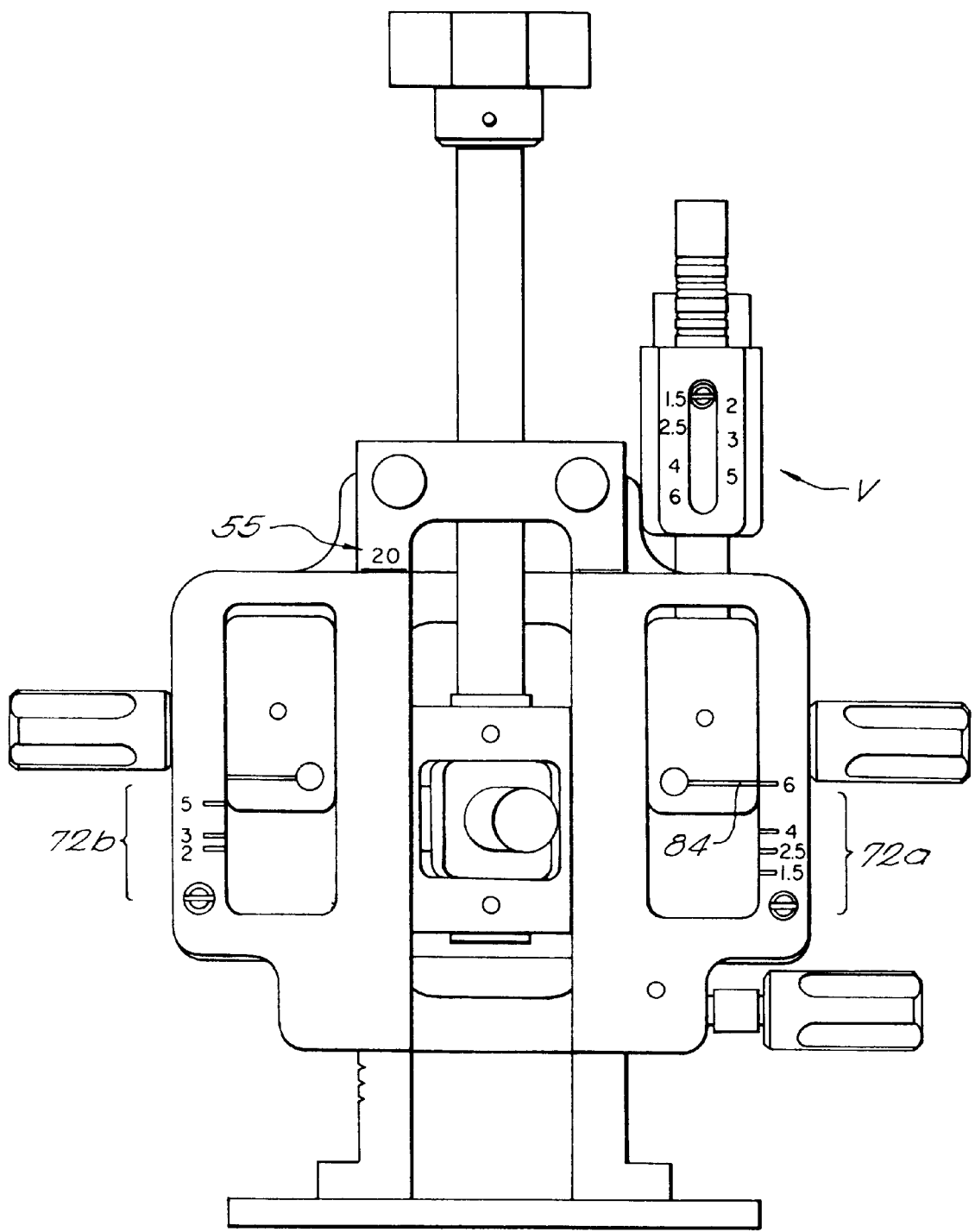
FIG. 4 is a face plan view thereof.

FIG. 4 is a frontal plan view, more clearly showing the various sets of graduations. These are used for setting the tissue balancing flexion gap with graduations 55, setting the femoral component size with the drill guide positioning template 80 and graduations 84, 72a and 72b confirming the size with the vertical and horizontal graduations V, H of the A/P positioning cortex hook assembly.

Figure 5:
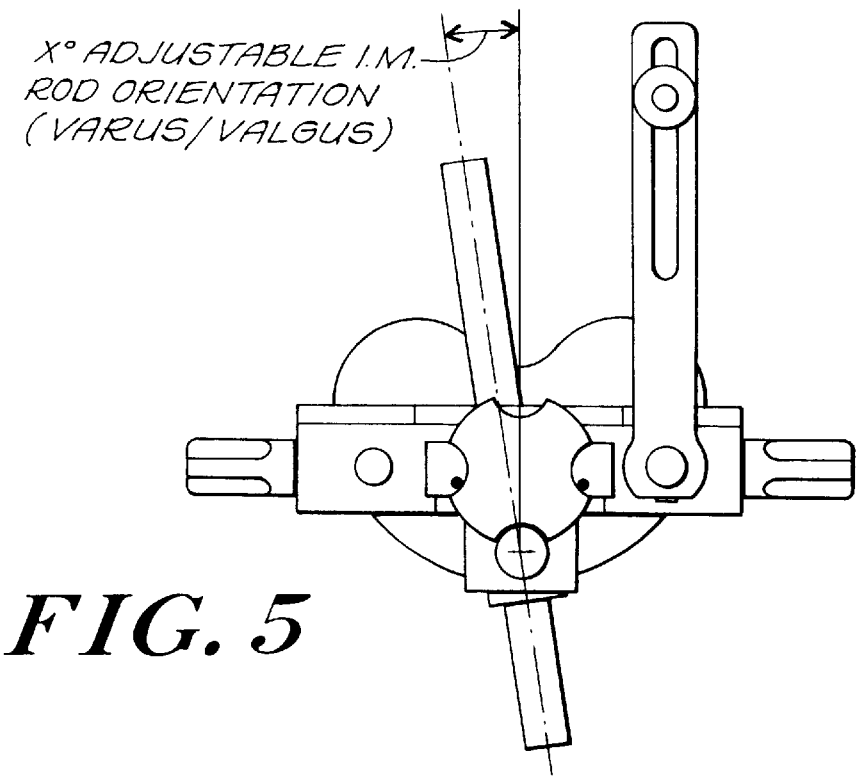
FIG. 5 is a top view thereof.

FIG. 5 is a top view more clearly illustrating the pivot range of adjustment to accommodate the orientation of the intramedullary rod, e.g. femoral axis, with respect to the other components of the tool, showing varus/valgus angle.

Figure 6:
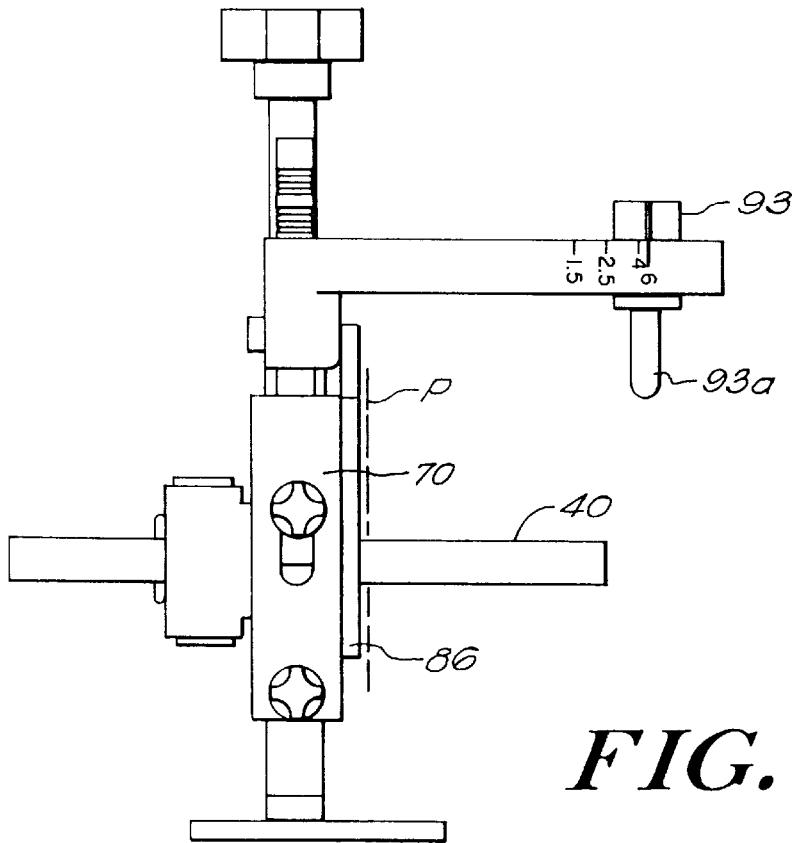
FIG. 6 is a side plan view.

FIG. 6 is a side plan view, illustrating the stylus tip 93a, the intramedullary rod 40, and the bridge plate 86 of the drill guide assembly (which rests against the plane "P" of the femoral end face) clarifing the spatial relation of these different sizing and positioning assemblies 70, 80 (FIG. 3) against the distal femur resected surface.

This completes a description of a basic embodiment of the tensioning and sizing tool of the present invention and its mode of use in setting the flexion gap, sizing the prosthetic component and adjusting soft tissue tension. It will be appreciated that by providing these three capabilities in a single instrument, numerous separate adjustments which need to refer to different landmarks and which require extensive time for setting up and repositioning the tools, are replaced, simplifying the overall procedure for preparing the bone to fit a prosthesis. Among the novel elements of the structure of the device, rather than separating the two resected bone ends with paddles or lifting one with a rod or torquing arrangement, the present invention advantageously provides a table or base which jacks up a carriage to support the intramedullary rod. This allows for a flexible extension of the femur, and permits several practical adjustments to be carried out with enhanced control or perception of the tensioning and positioning of necessary components.

The invention being thus disclosed in a representative prototype embodiment, further variations and modifications will occur to those skilled in the art, and all such variations and modifications are considered to be within the scope of the invention has set forth herein and defined by the claims appended hereto.

What is claimed is:

1. A tool for prosthetic joint replacement surgery, such tool comprising a jack for supporting a bone of an articulating set of bones to which a prosthetic end component is to be fastened at a respective end of said bone as it remains attached by ligaments to an opposed bone of said set, said jack including a jack assembly for raising said bone to permit the surgeon to adjust soft tissue tension in flexion, and support means raised by the jack assembly, said support means pivotally engaging and supporting said bone such that said bone rotates due to tension of said ligaments, and a jig carried on the jack. said jig including a template for placing an aligned mark to prepare said bone for fastening the prosthetic end component said jack cooperating with said jig to position the template while the bone has rotated into natural alignment, thereby assuring a correct rotational alignment of the bone when the prosthetic end component is attached.

2. A tool according to claim 1, wherein the jig includes a drill guide for positioning drill holes in an end surface of the bone to secure a cutting block.

3. A tool according to claim 1, wherein the jig and jack include scale markings that cooperate to indicate size of the component.

4. A tool according to claim 1, wherein the support means includes an intramedullary rod extending from the jack assembly into the bone such that the bone rotates about its longitudinal axis.

5. A tool according to claim 4, wherein the jig marks an orientation or position of a saw cut plate for fitting a femoral end component.

6. A tool according to claim 4, wherein the jack includes a gimballed assembly that engages the intramedullary rod to support the bone, and the back varies height of the gimballed assembly, thereby allowing the bone to assume a natural varus/valgus orientation.

* * * * *

UNITED STATES PATENT AND TRADEMARK OFFICE
CERTIFICATE OF CORRECTION

PATENT NO. : 6,056,756
DATED : May 2, 2000
INVENTOR(S) : Eng et al.

Page 1 of 1

It is certified that error appears in the above-identified patent and that said Letters Patent is hereby corrected as shown below:

<u>Column 6,</u>
Line 31, "and the back" should read -- and the jack --.

Signed and Sealed this

Twenty-third Day of April, 2002

Attest:

JAMES E. ROGAN
Attesting Officer     Director of the United States Patent and Trademark Office